United States Patent [19]
Miller

[11] Patent Number: 5,840,765
[45] Date of Patent: Nov. 24, 1998

[54] DEPILATING METHOD

[76] Inventor: Ethel Miller, 1408 Swan Ave., Yakima, Wash. 98902

[21] Appl. No.: 905,460

[22] Filed: Aug. 4, 1997

[51] Int. Cl.⁶ ..................................................... A61K 31/05
[52] U.S. Cl. ........................... 514/731; 514/736; 514/737
[58] Field of Search .................................... 514/731, 736, 514/737

[56] References Cited

U.S. PATENT DOCUMENTS

| | | |
|---|---|---|
| 707,954 | 8/1902 | Blinn . |
| 707,955 | 8/1902 | Blinn . |
| 3,865,546 | 2/1975 | Zemlin et al. ............................... 8/161 |
| 5,645,825 | 7/1997 | Hillebrand et al. ........................ 424/73 |

*Primary Examiner*—Leonard Schenkman
*Attorney, Agent, or Firm*—David L. Tingey

[57] ABSTRACT

A method of removal or retardation of growth of hair on the human body by application of phenol, a phenol derivative or a combination of at least two from the group of phenol and phenol derivatives. The element or combination is in the form of a liquid or paste and is applied to the skin and thereafter removed by cleansing. Hair growth is thereafter retarded or eliminated.

17 Claims, No Drawings

DEPILATING METHOD

FIELD OF THE INVENTION

The present invention relates generally to a method for hair removal and hair growth retardation and elimination and particularly to a method of hair removal and hair growth retardation and elimination from human skin.

BACKGROUND OF THE INVENTION

Methods and compositions are known in the prior art which act as a depilating agent or method regarding hair on human skin. U.S. Pat. No. 707,954 and 707,955 to Blinn discloses a depilating compound and a method of use regarding removal of hair from the human body. Other methods of hair removal are known including the use of wax. The patents referred to herein are provided herewith in an Information Disclosure Statement in accordance with 37 CFR 1.97.

SUMMARY OF THE INVENTION

The present invention discloses the use of phenol, phenol derivatives or a combination in liquid or paste form by application to the area of the human body from which hair is desired to be removed. The element or combination application is by exposure of the skin to the liquid, paste or salve generally through the use of a compress, bathing or rubbing or other means. The element or combination remains in contact with the skin for 10 minutes to several hours and is cleansed from the skin by washing with soap and water. Thereafter hair growth will be eliminated or retarded within the area of application.

DETAILED DESCRIPTION

The Depilating Method disclosed herein is directed to the reduction or elimination of growth of hair on the human body. FIG. 1 illustrates by a flow diagram the process claimed herein. The preferred embodiment of the invention is the method wherein phenol derivatives o-phenylphenol and chlorophene or chlorophenol are combined to compose 2% to 5% o-phenylphenol and 5% to 7% chlorophene or chlorophenol by volume. An alternative embodiment of the invention is the method wherein phenol, phenol combined with phenol derivatives or a combination of phenol derivatives compose 2% to 12% by volume of the composition. Phenol singularly, as the sole active ingredient or element, or phenol in combination with phenol derivatives or a combination of phenol derivatives, as a compound, will be formed into a liquid, paste or salve with other substances for the purpose of limiting the concentration of phenol and or phenol derivatives.

The hair, within the area to which the element or composition is to be applied, is removed by means, preferably with wax, within six hours prior to the application of the composition. The indicated element, combination or compound is applied as a liquid, paste or salve to the human body area from which hair and or hair follicles are desired to be removed. Application is by exposure, by means, of the skin and hence hair follicles, to the liquid, paste or salve. Means of application include swabbing the area of concern with a swab or compress containing or saturated with the composition, bathing or rubbing the area with the composition or other similar means of application of topical compositions to the human skin. Thereafter, the area is allowed to dry for approximately 10 minutes to several hours. The area is then washed, for example with warm soapy water, with the resulting retardation of growth or the elimination of growth of hair from the indicated portion of the human body. Alternative embodiments of the invention are realized by the use in the process of phenol separately and singularly, phenol in combination with one or more phenol derivatives or a combination of phenol derivatives. An embodiment of the composition to be employed in the process claimed herein is the combination of 2% to 5% o-phenylphenol, 5% to 7% chlorophene or chlorophenol combined with 50% to 70% water, 1% to 5% glycerine, 1% to 5% ethyl alcohol 0.5% to 3% isopropyl alcohol.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. A method of removing hair from the human body which comprises applying to the skin of said human body an effective amount of a composition consisting essentially of phenol, o-phenylphenol, or chlorophenol or mixtures thereof in an effective concentration.

2. The method of claim 1 wherein said composition is in the form of paste.

3. The method of claim 1 wherein said composition is in the form of a liquid.

4. The method of claim 1 wherein said composition is in the form of a wax.

5. The method of claim 1 wherein said composition is in the form of a salve.

6. The method of claim 1 wherein in the composition contains 2% to 5% of o-phenylphenol and 5% to 7% of chlorophenol by volume.

7. The method of claim 1 wherein said composition is diluted by water.

8. The method of claim 7 wherein said composition comprises 50% to 70% water.

9. The method of claim 1 wherein said composition further comprises of an effective amount of glycerine.

10. The method of claim 9 wherein said composition comprises 1% to 5% glycerine.

11. The method of claim 1 wherein said composition further comprises ethyl alcohol.

12. The method of claim 11 wherein said composition comprises 1–5% ethyl alcohol.

13. The method of claim 1 further comprising before the step of applying said composition to said human body, the step of first removing the hair from said human body by other means.

14. A method of retarding hair growth on a human body which comprises applying to an area of the skin of said human body an effective amount of a composition the essential component or components of which comprise phenol, o-phenylphenol, or chlorophenol or mixtures thereof.

15. A method of removing hair from the human body which comprises applying to the skin of said human body an effective amount of a composition consisting essentially of phenol, or derivatives of phenol, or mixtures thereof.

16. The method of claim 15 wherein said composition is diluted to form an effective concentration for application to said human body.

17. The method of claim 16 wherein said composition is diluted by water.

* * * * *